US009441965B1

(12) United States Patent
Gibson et al.

(10) Patent No.: US 9,441,965 B1
(45) Date of Patent: Sep. 13, 2016

(54) OCEANGRAPHIC ASSEMBLY FOR COLLECTING DATA ALONG MULTIPLE WATER COLUMNS

(71) Applicants: Robert P. Gibson, Panama City, FL (US); Joshua A. Lappen, Panama City, FL (US); Amanda Mackintosh, Panama City, FL (US); Jessica Haig, Panama City, FL (US); Robert S. Pagliari, Ft. Walton Beach, FL (US); Richard F. Paradis, Groton, CT (US)

(72) Inventors: Robert P. Gibson, Panama City, FL (US); Joshua A. Lappen, Panama City, FL (US); Amanda Mackintosh, Panama City, FL (US); Jessica Haig, Panama City, FL (US); Robert S. Pagliari, Ft. Walton Beach, FL (US); Richard F. Paradis, Groton, CT (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 195 days.

(21) Appl. No.: 13/930,023

(22) Filed: Jun. 28, 2013

(51) Int. Cl.
    *G01C 13/00* (2006.01)
(52) U.S. Cl.
    CPC ..................... *G01C 13/00* (2013.01)
(58) Field of Classification Search
    None
    See application file for complete search history.

(56) References Cited

U.S. PATENT DOCUMENTS

| 4,258,568 | A  | * | 3/1981  | Boetes et al. | 73/170.11 |
|-----------|----|---|---------|---------------|-----------|
| 5,894,450 | A  | * | 4/1999  | Schmidt et al. | 367/134 |
| 7,649,803 | B2 | * | 1/2010  | Ray et al. | 367/15 |
| 2003/0179652 | A1 | * | 9/2003 | Desa et al. | 367/131 |
| 2007/0113687 | A1 | * | 5/2007 | Sauter | 73/864.66 |
| 2008/0056066 | A1 | * | 3/2008 | George et al. | 367/20 |
| 2010/0308589 | A1 | * | 12/2010 | Rohrer | 290/53 |
| 2013/0013212 | A1 | * | 1/2013 | Hatchell et al. | 702/14 |
| 2014/0214323 | A1 | * | 7/2014 | Gould et al. | 702/2 |
| 2015/0003194 | A1 | * | 1/2015 | Brizard | 367/15 |

* cited by examiner

*Primary Examiner* — Andre Allen
(74) *Attorney, Agent, or Firm* — James T. Shepherd

(57) ABSTRACT

An apparatus collects data along water columns. A telescoping shell has an outer cylinder and an inner cylinder. An expansible chamber is defined within the outer cylinder. A fluid flow path is formed between the expansible chamber and the outer cylinder's open end. A gas source is vented to the expansible chamber. Sensors, including a pressure sensor, are coupled to the shell such that they are exposed to an ambient water environment when the apparatus is deployed therein. A vent mounted in the outer cylinder vents the expansible chamber to the ambient water environment. A controller controls the gas source and vent based on sensed pressure of the ambient water environment such that water from the ambient water environment is admitted to or expelled from the expansible chamber via the fluid flow path.

19 Claims, 2 Drawing Sheets

OCEANOGRAPHIC ASSEMBLY FOR COLLECTING DATA ALONG MULTIPLE WATER COLUMNS

ORIGIN OF THE INVENTION

The invention described herein may be manufactured and used by or for the Government of the United States of America for Governmental purposes without payment of any royalties.

FIELD OF THE INVENTION

The invention relates generally to collecting environmental data from water columns, and more particularly to an assembly that can autonomously collect environmental data from a plurality of water columns in a body of water.

BACKGROUND OF THE INVENTION

Scientists have traditionally relied on expensive manned expedition and research cruises to collect oceanographic data. More recently, unmanned underwater vehicles (UUVs) have been employed to collect oceanographic data. While the use of UUVs is less expensive than manned expeditions, UUVs are still relatively expensive. Further, UUVs are typically designed to operate in horizontal planes. Accordingly, using a UUV to collect oceanographic data in a vertical water column involves complex and time-consuming UUV navigation.

SUMMARY OF THE INVENTION

Accordingly, it is an object of the present invention to provide an apparatus that can collect oceanographic data.

Another object of the present invention is to provide an apparatus that can collect oceanographic data on a vertical column of water.

Still another object of the present invention is to provide an apparatus that operates autonomously to collect oceanographic data on multiple vertical columns of water.

Other objects and advantages of the present invention will become more obvious hereinafter in the specification and drawings.

In accordance with the present invention, an apparatus is provided for collecting data along multiple water columns. A telescoping shell is defined by (i) an outer cylinder having a closed end and an open end, and (ii) an inner cylinder fitted in and extendible from the outer cylinder's open end. The inner cylinder has an outer diameter that is less than a diameter of the open end of the outer cylinder. The inner cylinder also has a piston formed at one longitudinal end thereof that resides in the outer cylinder. The inner cylinder further has a cap formed at an opposing longitudinal end thereof. The piston has a diameter that is greater than the diameter of the outer cylinder's open end and less than an inside diameter of the outer cylinder. As a result, an expansible chamber is defined within the outer cylinder with the piston forming a movable wall thereof. Further, a fluid flow path is formed between the expansible chamber and the outer cylinder's open end. A gas source is disposed in the inner cylinder and is vented through the piston into the expansible chamber such that a gas can be dispensed from the gas source into the expansible chamber. Sensors are coupled to the shell such that they are exposed to an ambient water environment when the oceanographic assembly is deployed therein. The sensors include a pressure sensor. A controllable vent is mounted in the outer cylinder such that it can vent the expansible chamber to the ambient water environment when the vent, is open. A controller is coupled to the sensors, the gas source and the vent. The controller controls the gas source and vent based on pressure of the ambient water environment sensed by the pressure sensor such that water from the ambient water environment is one of admitted to and expelled from the expansible chamber via the fluid flow path.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
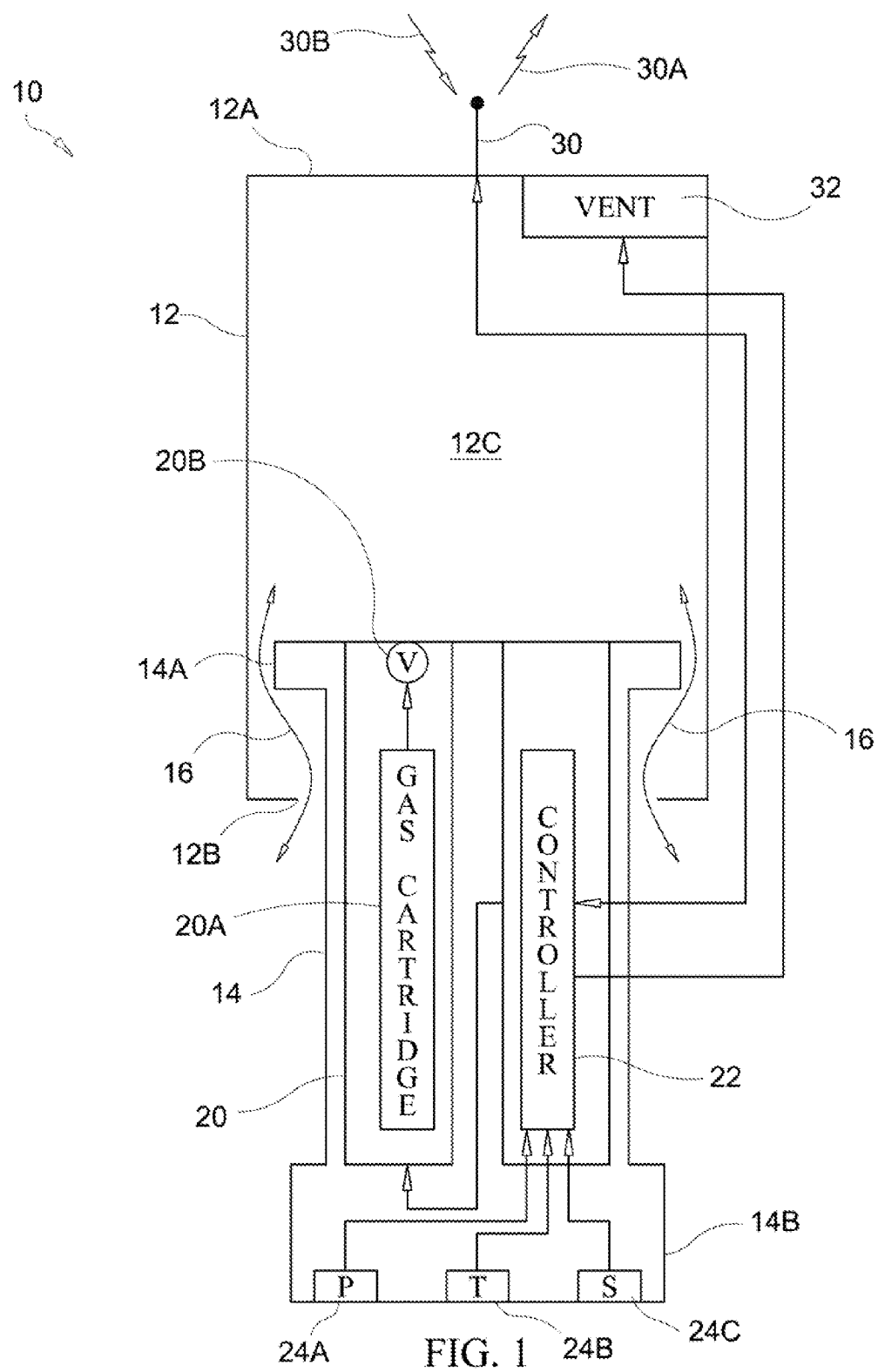
FIG. 1 is a schematic view of an apparatus for collecting data along multiple water columns in accordance with an embodiment of the present invention.

Referring now to the drawings and more particularly to FIG. 1, an apparatus for collecting oceanographic data along one or more vertical water columns is shown and is referenced generally numeral 10. Apparatus 10 is an unmanned system that can be deployed in a water environment by an aircraft or watercraft. Apparatus 10 is illustrated in its post-deployed state in order to more clearly illustrate the feature thereof.

Apparatus 10 includes an outer shell that telescopes from a pre-deployed position to the illustrated post-deployed position. The outer shell includes an outer cylinder 12 and an inner cylinder 14 that fits in and is extendible from outer cylinder 12. Outer cylinder 12 has a closed end 12A and an open end 12B. Inner cylinder 14 has a piston 14A formed at one end thereof and a cap 14B formed at the opposing end thereof. For purposes of the present invention, dimensional relationships between outer cylinder 12 and inner cylinder 14 include the following:

(i) the outer diameter of inner cylinder 14 is less than the diameter of open end 12B; and (ii) the diameter of piston 14A is greater than the diameter of open end 12B and less than the inner diameter of outer cylinder 12.

The differences between the various diameters noted above are on the order of millimeters. By virtue of these dimensional relationships, inner cylinder 14 can move axially in and out of outer cylinder 12. When apparatus 10 is in its post-deployed position with piston 14A displaced axially from closed end 12A, a chamber 12C is defined in outer cylinder 12. Since inner cylinder 14 can move axially into or out of outer cylinder 12, chamber 12C is an expansible chamber with piston 14A forming a movable wall thereof. In addition, the above-defined dimensional relationships provide for the creation of a fluid flow path between chamber 12C and open end 12B. This fluid flow path is referenced in FIG. 1 by flow lines 16. The arrows at either end of flow lines 16 indicate that fluid can flow in either direction depending on the operational state of apparatus 10 as will be described further below.

Disposed within inner cylinder 14 are a gas source 20 and a controller 22. A number of sensors are also provided on apparatus 10 for collecting oceanographic data. Such sensors can be mounted on (or in) cap 14B or elsewhere on the outer shell of apparatus 10 without departing from the scope of the present invention. Such sensors may include a pressure sensor ("P") 24A, a temperature sensor ("T") 24B, and salinity sensor ("S") 24C. These three sensors form the basis of a "conductivity, temperature and depth" (CTD) sensing package as is known in the art. Disposed within (or on) outer cylinder 12 at (or near) closed end 12B are an antenna 30 and a controllable gas vent 32. Controller 22 is coupled to gas source 20, sensors 23A-24C, antenna 30 and gas vent 32 for the control thereof or to receive signals/data therefrom as will be explained further below. For clarity of illustration only, signal lines coupling controller 22 to antenna 30 and gas vent 32 are depicted outside of apparatus 10.

Gas source 20 is vented into chamber 12C through piston 14A. Gas source 20 is any controllable structure or system that can supply a gas under pressure to chamber 12C when "instructed" to do so by controller 22. By way of example, gas source 20 can include a pressurized cartridge 20A of an inert gas (e.g., carbon dioxide) and a valve 203 (e.g., a solenoid valve). Although only one cartridge 20A is shown, it is to be understood that multiple cartridges can be provided without departing from the scope of the present invention.

Antenna 30 is any antenna structure or system that can transmit signals 30A and receive signals 30B over the airwaves. For example, antenna 30 can be configured to receive GPS signals from GPS satellites (not shown) and configured to transmit data supplied thereto by controller 22. The particular design and construction of antenna 30 is not a limitation of the present invention. Gas vent 32 is any controllable structure or system that can be opened to vent chamber 12C to an ambient environment or closed to prevent such venting.

Figure 2:
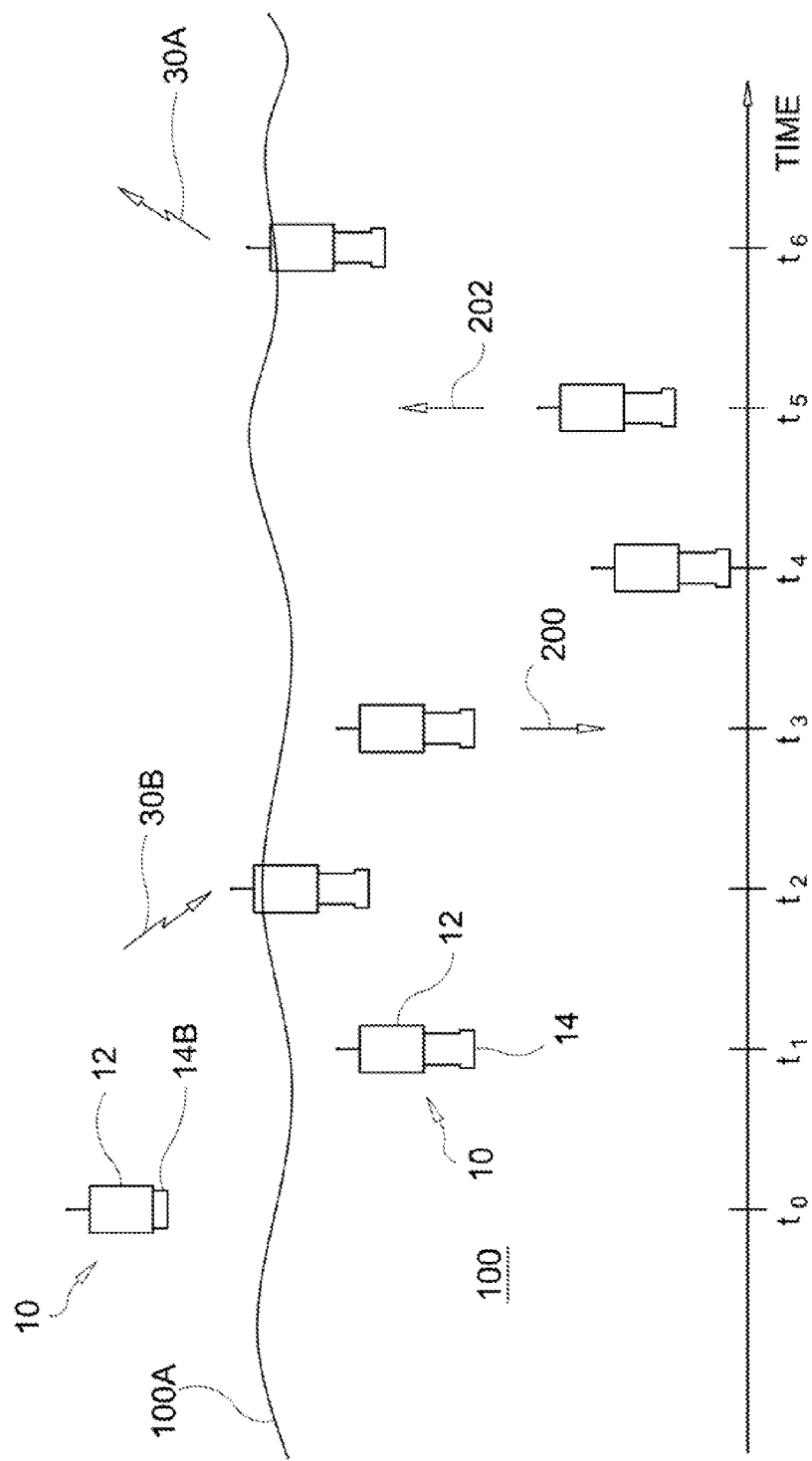
FIG. 2 is a schematic view of an operational sequence for the apparatus once it is deployed in a water environment in accordance with an embodiment of the present invention.

Referring additionally now to FIG. 2, an operational sequence for apparatus 10 in accordance with an embodiment of the present invention is illustrated along with a timeline. At time $t_0$, apparatus 10 is in the air just above the surface 100A of a water environment 100. (Apparatus 10 could also be released within water 100 without, departing from the scope of the present invention.) In this pre-deployed state, inner cylinder 14 resides within outer cylinder 12 such that cap 14B adjoins outer cylinder 12. At time $t_1$, apparatus 10 is in water 100 whereby controller 22 closes gas vent 32 and controls gas source 20 such that gas is expelled into chamber 12C causing chamber 12C to fill/expand with the gas thereby causing inner cylinder 14 to telescope from outer cylinder 12 to its state shown in FIG. 1. The gas filling chamber 12C makes apparatus 10 buoyant, so that it rises to the water's surface 100A at time $t_2$ where it can receive signals 30B such as GPS signals. At surface 100A, pressure sensor 24A provides pressure data to controller 22. The surface pressure measurement is used by controller 22 to open gas vent. 32 while controlling gas source 20 to prevent gas from being pumped into chamber 12C. As a result, gas in chamber 12C vents to the surrounding environment as water 100 is admitted into chamber 22C along fluid flow path 16. As a result, apparatus 10 loses its buoyancy and sinks (as indicated by arrow 200) through a vertical water column at time $t_3$. As apparatus 10 sinks, controller 22 collects data sensed by sensors 24A-24C.

At time $t_4$, apparatus 10 has sunk to a predetermined depth as indicated by the pressure sensed by pressure sensor 24A. In response to this pressure measurement, controller 22 closes gas vent 32 and controls gas source 20 to expel gas into chamber 12C thereby driving a sufficient amount of water therefrom along fluid flow path 16. This process continues until apparatus 10 is again buoyant at time $t_5$. When this occurs, apparatus 10 floats up to surface 100A (as indicated by arrow 202) and can again collect data from sensor 23A-24C. At time $t_6$, apparatus 10 is at surface 100A where controller 22 can provide sensed data to antenna 30 along with the GFS position of apparatus 10 for transmission as signals 30A. Controller 22 could collect new GPS signals 30B before repeating the above-described sequence for another data collection sequence associated with another vertical water column.

The advantages of the present invention are numerous. The apparatus is a simple unmanned device that can operate autonomously to collect and transmit oceanographic data from multiple water columns. The apparatus does not require any propulsion or navigation systems. The sensed data can be correlated with GPS location to provide water column data at specific geographic locations.

Although the invention has been described relative to specific embodiments thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. An apparatus for collecting data along multiple water columns, comprising:
   a telescoping shell defined by (i) an outer cylinder having a closed end and an open end, and (ii) an inner cylinder fitted in and extendible from said open end of said outer cylinder, said inner cylinder having an outer diameter that is less than a diameter of said open end, said inner cylinder having a piston formed at one longitudinal end thereof and residing in said outer cylinder, said inner cylinder further having a cap formed at an opposing longitudinal end thereof, said piston having a diameter that is greater than said diameter of said open end and less than an inside diameter of said outer cylinder, wherein an expansible chamber is defined within said outer cylinder with said piston forming a movable wall thereof;
   a gas source containing a pressurized gas disposed in said inner cylinder;
   a controllable valve disposed between said gas source and said expansible chamber, said valve operable to vent said gas from said gas source into said expansible chamber;
   a plurality of sensors coupled to said shell and adapted to be exposed to an ambient water environment when the apparatus is deployed therein, said plurality of sensors including a pressure sensor;
   a controllable vent mounted in said outer cylinder and adapted to vent said expansible chamber to the ambient water environment when said vent is opened; and
   a controller coupled to said sensors, said valve and said vent, said controller operable to close said vent and control said valve to expel said gas from said gas source into said expansible chamber at a first pressure sensed by said pressure sensor, and said controller operable to open said vent and control said valve to prevent expulsion of said gas from said gas source into said expansible chamber at a second pressure sensed by said pressure sensor.

2. An apparatus as in claim 1, further comprising an antenna mounted at said closed end of said outer cylinder and coupled to said controller, said antenna adapted to receive and transmit signals through the air.

3. An apparatus as in claim 1, wherein said plurality of sensors further include at least one sensor selected from the group consisting of a temperature sensor and a salinity sensor.

4. An apparatus as in claim 1, wherein said gas source includes a structure for storing said gas under pressure.

5. An apparatus as in claim 1, wherein said gas source includes at least one cartridge filled with pressurized carbon dioxide.

6. An apparatus as in claim 1 wherein, prior to deployment in the ambient water environment, said inner cylinder is fitted fully within said outer cylinder with said cap adjoining said outer cylinder and wherein, immediately after deployment in the ambient water environment, said controller expels said gas into said expansible chamber.

7. An apparatus as in claim 2, wherein said controller collects data from said sensors, and wherein said controller provides said data to said antenna.

8. An apparatus for collecting data along multiple water columns, comprising:
    a telescoping shell defined by (i) an outer cylinder having a closed end and an open end, and (ii) an inner cylinder fitted in and extendible from said open end of said outer cylinder;
    said inner cylinder having an outer diameter that is less than a diameter of said open end, said inner cylinder having a piston formed at one longitudinal end thereof and residing in said outer cylinder, said inner cylinder further having a cap formed at an opposing longitudinal end thereof, said piston having a diameter that is greater than said diameter of said open end and less than an inside diameter of said outer cylinder, wherein an expansible chamber is defined within said outer cylinder with said piston forming a movable wall thereof, and wherein a fluid flow path is formed between said expansible chamber and said open end;
    a gas source containing a pressurized gas disposed in said inner cylinder;
    a controllable valve disposed between said gas source and said expansible chamber, said valve operable to vent said gas from said as source into said expansible chamber;
    a plurality of sensors coupled to said shell and adapted to be exposed to an ambient water environment when the apparatus is deployed therein, said plurality of sensors including a pressure sensor;
    a controllable vent mounted in said outer cylinder and adapted to vent said expansible chamber to the ambient water environment when said vent is opened; and
    a controller coupled to said sensors, said gas source and said vent, said controller operable to control said valve and said vent based on pressure of the ambient water environment sensed by said pressure sensor, wherein water from the ambient water environment is one of admitted to and expelled from said expansible chamber via said fluid flow path.

9. An apparatus as in claim 8, further comprising an antenna mounted at said closed end of said outer cylinder and coupled to said controller, said antenna adapted to receive and transmit signals through the air.

10. An apparatus as in claim 8, wherein said plurality of sensors further include at least one sensor selected from the group consisting of a temperature sensor and a salinity sensor.

11. An apparatus as in claim 8, wherein said gas source includes a structure for storing said gas under pressure.

12. An apparatus as in claim 8, wherein said gas source includes at least one cartridge filled with pressurized carbon dioxide.

13. An apparatus as in claim 8 wherein, prior to deployment in the ambient water environment, said inner cylinder is fitted fully within said outer cylinder with said cap adjoining said outer cylinder and wherein, immediately after deployment in the ambient water environment, said controller expels said gas into said expansible chamber.

14. An apparatus as in claim 9, wherein said controller collects data from said sensors, and wherein said controller provides said data to said antenna.

15. An apparatus for collecting data along multiple water columns, comprising:
    a telescoping shell defined by (i) an outer cylinder having a closed end and an open end, and (ii) an inner cylinder fitted in and extendible from said open end of said outer cylinder, said inner cylinder having an outer diameter that is less than a diameter of said open end, said inner cylinder having a piston formed at one longitudinal end thereof and residing in said outer cylinder, said inner cylinder further having a cap formed at an opposing longitudinal end thereof, said piston having a diameter that is greater than said diameter of said open end and less than an inside diameter of said outer cylinder, wherein an expansible chamber is defined within said outer cylinder with said piston forming a movable wall thereof;
    a gas source containing a pressurized gas in said inner cylinder;
    a controllable valve disposed between said gas source and said expansible chamber, said valve operable to vent said gas from said gas source into said expansible chamber;
    a plurality of sensors coupled to said shell and adapted to be exposed to an ambient water environment when the apparatus is deployed therein, said plurality of sensors including a pressure sensor, a temperature sensor, and a salinity sensor;
    a controllable vent mounted in said outer cylinder and adapted to vent said expansible chamber to the ambient water environment when said vent is opened;
    a controller coupled to said sensors, said valve and said vent, said controller operable to close said vent and control said valve to expel said gas from said gas source into said expansible chamber at a first pressure sensed by said pressure sensor, and said controller operable to open said vent and control said valve to prevent expulsion of said gas from said gas source into said expansible chamber at a second pressure sensed by said pressure sensor; and
    an antenna mounted at said closed end of said outer cylinder and coupled to said controller, said antenna adapted to receive and transmit signals through the air.

16. An apparatus as in claim 15, wherein said gas source includes a structure for storing said gas under pressure.

17. An apparatus as in claim 15, wherein said gas source includes at least one cartridge filled with pressurized carbon dioxide.

18. An apparatus as in claim 15 wherein, prior to deployment in the ambient water environment, said inner cylinder is fitted fully within said outer cylinder with said cap adjoining said outer cylinder and wherein, immediately after deployment in the ambient water environment, said controller expels said gas into said expansible chamber.

19. An apparatus as in claim 15, wherein said controller collects data from said sensors, and wherein said controller provides said data to said antenna.

\* \* \* \* \*